United States Patent [19]

Koyama et al.

[11] Patent Number: 5,565,557
[45] Date of Patent: Oct. 15, 1996

[54] PROCESS FOR PRODUCING SUCROSE FATTY ACID ESTER

[75] Inventors: Yasuaki Koyama, Shiga; Nobuyuki Kawase, Tokyo; Hiroshi Yamamoto, Mie; Shigetomi Kawata, Mie; Yukio Kasori, Mie, all of Japan

[73] Assignee: Mitsubishi Chemical Corporation, Tokyo, Japan

[21] Appl. No.: 362,932

[22] Filed: Dec. 23, 1994

[30] Foreign Application Priority Data

Dec. 24, 1993 [JP] Japan .................................. 5-328449

[51] Int. Cl.$^6$ .............................. C13K 5/00; C13K 7/00
[52] U.S. Cl. ....................... 536/123.13; 536/127
[58] Field of Search ................... 536/123.13, 127

[56] References Cited

U.S. PATENT DOCUMENTS

| | | | |
|---|---|---|---|
| 3,054,789 | 9/1962 | D'Amato | 536/119 |
| 4,983,731 | 1/1991 | Wagner et al. | 536/127 |
| 4,995,911 | 2/1991 | Matsumoto et al. | 127/48 |
| 4,996,309 | 2/1991 | Matsumoto et al. | 536/119 |
| 5,008,387 | 4/1991 | Matsumoto et al. | 536/119 |
| 5,011,922 | 4/1991 | Matsumoto et al. | 536/119 |
| 5,017,697 | 5/1991 | Matsumoto et al. | 536/127 |
| 5,378,834 | 1/1995 | Koerts et al. | 536/127 |

FOREIGN PATENT DOCUMENTS

| | | |
|---|---|---|
| 2004899 | 9/1970 | Germany . |
| 2041932 | 3/1971 | Germany . |
| 48021927 | 5/1969 | Japan . |
| 50-105610 | 8/1975 | Japan . |
| 50-130712 | 10/1975 | Japan . |
| 51-029417 | 3/1976 | Japan . |
| 57-128652 | 8/1982 | Japan . |
| 62-129294 | 6/1987 | Japan . |
| 63-027497 | 2/1988 | Japan . |
| 2040392 | 2/1990 | Japan . |
| 2056495 | 2/1990 | Japan . |
| 2152986 | 6/1990 | Japan . |
| 402152986 | 6/1990 | Japan . |
| 3011093 | 1/1991 | Japan . |
| 4246890 | 8/1992 | Japan . |
| 6122694 | 5/1994 | Japan . |
| 6336493 | 12/1994 | Japan . |
| 826801 | 1/1960 | United Kingdom . |

OTHER PUBLICATIONS

Perry et al., *Chemical Engineer's Handbook*, Fifth Ed., McGraw–Hill Book Co., New York, NY, 1973, pp. 21–23 to 21–29, see especially pp. 21–23 to 21–24.

*Primary Examiner*—John Kight
*Assistant Examiner*—L. Eric Crane
*Attorney, Agent, or Firm*—Sughrue, Mion, Zinn, Macpeak & Seas

[57] ABSTRACT

A process for producing a sucrose fatty acid ester wherein the sucrose fatty acid ester is recovered from a reaction mixture prepared by reacting sucrose with a fatty acid alkyl ester in the presence of an alkali catalyst by using dimethyl sulfoxide as a reaction solvent, the process comprising: (i) subjecting the reaction mixture to a first liquid-liquid extraction by using a hardly water-miscible organic solvent, which is selected from an alcohol having at least 4 carbon atoms and a ketone having at least 4 carbon atoms, and water as extractants, with regulating the pH value of an aqueous phase to 3 to 7.5, to thereby extract dimethyl sulfoxide in the reaction mixture into the aqueous phase, and the sucrose fatty acid ester into an organic solvent phase; (ii) subjecting an organic solvent solution containing the sucrose fatty acid ester thus obtained as the organic solvent phase in the first liquid-liquid extraction to a second liquid-liquid extraction by a continuous counter-current system using water, to thereby extract dimethyl sulfoxide remaining in the organic solvent solution into an aqueous phase, thus giving an organic solvent solution which is substantially free from dimethyl sulfoxide; and (iii) recovering the sucrose fatty acid ester from the organic solvent solution.

20 Claims, No Drawings

PROCESS FOR PRODUCING SUCROSE FATTY ACID ESTER

FIELD OF THE INVENTION

This invention relates to a process for producing a sucrose fatty acid ester (hereinafter referred to simply as SE). More particularly, it relates to an industrial purification process by which an SE having a high purity can be industrially advantageously and stably obtained from a reaction mixture containing the SE, which has been prepared by the solvent method.

BACKGROUND OF THE INVENTION

SE has been employed as additives for various products including foods, cosmetics, drugs, dish detergents, feeds and resins, because of its excellent surface-activating performance, biodegradability and stability. In the field of the chemical industry, these compounds are highly useful as reaction aids in, for example, polymerization and oxidization.

Examples of a known method for producing an SE include one described in JP-B-35-13102 (the term "JP-B" as used herein means an "examined Japanese patent publication"), wherein sucrose undergoes an ester exchange reaction with a fatty acid ester such as a fatty acid methyl ester in a reaction solvent such as N,N-dimethylformamide or dimethyl sulfoxide (hereinafter referred to simply as DMSO) in the presence of an alkali catalyst.

The reaction mixture obtained by the above-mentioned method contains the reaction solvent, the unreacted sucrose, the alkali catalyst, etc. in addition to the SE product. There have been proposed several methods for separating the SE from this mixture (as described in JP-B-48-21927, JP-B-48-35049, JP-A-50-29417, JP-A-50-130712, etc.; the term "JP-A" as used herein means an "unexamined published Japanese patent application"). Usually, the mixture is subjected to liquid-liquid extraction with the use of an organic solvent (for example, hexane, butyl alcohol, methyl ethyl ketone, ethyl isobutyl ketone) and water. Thus the SE migrates mainly into the organic solvent phase, while the unreacted sucrose and the reaction solvent migrate into the aqueous phase. The organic solvent phase is then separated from the aqueous phase and the organic solvent is removed from the organic solvent phase containing the SE by, for example, distillation. Thus the SE can be recovered.

However the above-mentioned method can hardly be put into industrial use, because it suffers from a number of problems including the occurrence of hydrolysis of the SE in the liquid-liquid extraction, the migration of the SE into the aqueous phase, and the insufficient formation of the interface in the extraction. Also, it is difficult to obtain a highly pure SE by this method.

SUMMARY OF THE INVENTION

An object of the present invention is to provide a process for industrial purification of SE whereby the unreacted sucrose and DMSO can be efficiently separated and recovered from a reaction mixture, which has been prepared by producing an SE in a DMSO solvent, and thus the SE having a high purity can be industrially advantageously and stably produced.

Other objects and effects of the present invention will be apparent from the following description.

Under these circumstances, the present inventors have conducted extensive studies on a method for efficiently recovering an SE from a reaction mixture which has been prepared by performing an ester exchange reaction between sucrose with a fatty acid ester in a DMSO solvent in the presence of an alkali catalyst. As a result, they have successfully found out that an SE can be easily separated from DMSO and the unreacted sucrose while suppressing the decomposition of the SE by regulating the pH value of the aqueous phase within a specific range and that a highly pure SE contaminated with 1 ppm or less of DMSO can be easily recovered by combining specific extraction steps. The present invention has been completed based on these findings.

The present invention relates to a process for producing a sucrose fatty acid ester wherein the sucrose fatty acid ester is recovered from a reaction mixture prepared by reacting sucrose with a fatty acid alkyl ester in the presence of an alkali catalyst by using dimethyl sulfoxide as a reaction solvent, the process comprising:

(i) subjecting the reaction mixture to a first liquid-liquid extraction by using a hardly water-miscible organic solvent, which is selected from an alcohol having at least 4 carbon atoms and a ketone having at least 4 carbon atoms, and water as extractants, with regulating the pH value of an aqueous phase to 3 to 7.5, to thereby extract dimethyl sulfoxide in the reaction mixture into the aqueous phase, and the sucrose fatty acid ester into an organic solvent phase;

(ii) subjecting an organic solvent solution containing the sucrose fatty acid ester thus obtained as the organic solvent phase in the first liquid-liquid extraction to a second liquid-liquid extraction by a continuous counter-current system using water, to thereby extract dimethyl sulfoxide remaining in the organic solvent solution into an aqueous phase, thus giving an organic solvent solution which is substantially free from dimethyl sulfoxide; and (iii) recovering the sucrose fatty acid ester from the organic solvent solution.

DETAILED DESCRIPTION OF THE INVENTION

According to the present invention, when an SE is to be separated and recovered from a reaction mixture which has been prepared by reacting sucrose with a fatty acid alkyl ester in a DMSO solvent in the presence of an alkali catalyst, the reaction mixture is subjected to the first liquid-liquid extraction by using an organic solvent comprising an alcohol having at least 4 carbon atoms or a ketone having at least 4 carbon atoms and water as extractants, with regulating the pH value of the aqueous phase to 3 to 7.5. Thus the SE is extracted into the organic solvent phase while DMSO and the unreacted sucrose are extracted into the aqueous phase.

The organic solvent solution containing the SE thus obtained in the first liquid-liquid extraction is then subjected to the second liquid-liquid extraction of the continuous counter-current system with the use of water as an extractant. Thus DMSO and the unreacted sucrose contaminating the organic solvent solution are extracted into the aqueous phase. Then the organic solvent is removed from the organic solvent solution, which is substantially free from DMSO, obtained by the second liquid-liquid extraction to thereby give the target SE of a high purity.

Examples of the fatty acid alkyl ester to be used in the reaction with sucrose in the present invention include a $C_1$ to $C_4$ alkyl ester of a saturated or unsaturated fatty acid having 6 to 30 carbon atoms, which can be obtained from saturated or unsaturated fatty acids generally having 6 to 30, preferably 8 to 22, carbon atoms (for example, saturated fatty acids such as caproic acid, capric acid, lauric acid, myristic acid, palmitic acid, stearic acid, and behenic acid; and unsaturated fatty acids such as linoleic acid, oleic acid, linolenic acid, erucic acid and ricinoleic acid) and lower aliphatic alcohols having 1 to 4 carbon atoms (for example, methanol, ethanol, propanol, and butanol). Either one of these fatty acid alkyl esters or a mixture composed of these esters at an arbitrary ratio may be used. The fatty acid alkyl ester is employed generally in an amount of from 0.1 to 20 mol, preferably from 0.2 to 8 mol, per mol of sucrose.

DMSO is used as the reaction solvent by taking its heat stability, the solubility of sucrose therein, and the safety into consideration. The reaction solvent is employed generally in an amount of from 20 to 150% by weight, preferably from 30 to 80% by weight, based on the total amount of sucrose and the fatty acid alkyl ester.

The reaction is performed in the presence of an alkali catalyst. Since the reaction system is substantially nonaqueous, the alkali catalyst exists in the reaction system in a suspended state. Examples of the alkali catalyst include alkali metal hydrides, alkali metal hydroxides, and alkali metal salts of weak acids. In particular, alkali metal carbonates (for example, potassium carbonate and sodium carbonate) and alkali metal hydroxides are preferable therefor. The alkali catalyst is employed generally in an amount of from 0.001 to 0.1 equivalent to the fatty acid alkyl ester.

The reaction temperature is generally from 40° to 170° C., preferably from 60° to 150° C. The reaction pressure is generally from 0.2 to 43 KPa, preferably from 0.7 to 32 KPa. It is preferred that the reaction between sucrose and the fatty acid alkyl ester is performed under reflux of the reaction solvent, since an alcohol by-produced during the reaction can be easily removed from the reaction system thereby. The reaction time is generally from about 1 to 10 hours, though it varies depending on the amounts of the starting materials and the target SE.

Since sucrose carries 8 hydroxyl groups in its molecule, the sucrose fatty acid ester thus formed is in the form of a mixture composed of monoesters to octaesters. The composition of the ester product can be controlled by adjusting the ratio of the starting materials.

The reaction mixture of sucrose with the fatty acid ester thus obtained contains DMSO as the reaction solvent, the unreacted materials, the alkali catalyst, etc. in addition to the target SE. In the present invention, an SE of a high purity is recovered from this reaction mixture at a high yield.

In the present invention, the reaction mixture is subjected to the first liquid-liquid extraction by using a hardly water-miscible organic solvent and water under a specific pH condition. Thus the SE in the reaction mixture is extracted into the organic solvent phase while DMSO, the unreacted sucrose, etc. are extracted into the aqueous phase.

When the DMSO concentration in the reaction mixture is excessively high in this liquid-liquid extraction, the DMSO is liable to insufficiently migrate into the aqueous phase.

When the reaction mixture contains DMSO at a high concentration, therefore, it is preferable to previously distill off some portion of the DMSO to thereby control the its concentration. DMSO may be distilled off by, for example, using a film evaporator under reduced pressure at a temperature of from 60° to 150° C.

Alternatively, the DMSO concentration in the reaction mixture may be regulated to the desired range by decreasing the amount of the DMSO being under reflux at the last stage of the reaction between sucrose and the fatty acid alkyl ester. It is preferable that the concentration of DMSO in the reaction mixture, which is to be extracted, is from 10 to 80% by weight, more preferably from 20 to 50% by weight.

At the extraction, the pH value of the aqueous phase should be regulated to 3 to 7.5. When the liquid-liquid extraction is performed without neutralizing the alkali catalyst remaining in the reaction mixture, the pH value of the aqueous phase becomes 8 or above. In the present invention, hydrolysis of the SE during the extraction can be suppressed and thus the efficiency of the extraction of the SE into the organic solvent phase and the partition of the organic solvent phase from the aqueous phase can be improved by regulating the pH value within such a specific range. When the pH value is excessively high, the SE is liable to undergo hydrolysis and a high partition ratio of the SE into the organic solvent phase cannot be achieved. When the pH value is excessively low, on the other hand, the unreacted sucrose and DMSO become unstable.

The pH value at the extraction preferably ranges from 3 to 7.0, more preferably from 4 to 6.5. The pH value at the extraction may be regulated by previously adding an acid to the reaction mixture. Alternatively, the reaction mixture may be mixed with an aqueous solution of an acid and the organic solvent to thereby regulate the pH value.

The organic solvent comprising an alcohol or a ketone to be used in the extraction is a hardly water-miscible one having 4 or more, preferably 4 to 10, carbon atoms. Examples thereof include n-butanol, isobutanol, t-butanol, n-amyl alcohol, isoamyl alcohol, n-hexanol, cyclohexanol, methyl ethyl ketone, diethyl ketone, and methyl isobutyl ketone. Among these solvents, n-butanol and isobutanol are particularly preferable.

The organic solvent is generally used in an amount of from 0.5 to 20 parts by weight, preferably from 1 to 10 parts by weight, per part by weight of the SE in the reaction mixture. Water is generally employed in an amount of from 0.05 to 10 parts by weight, preferably from 0.5 to 2 parts by weight, per part by weight of the organic solvent. For example, it is preferable to perform the first liquid-liquid extraction by using water in an amount 1 to 10 times by weight as much as the SE in the reaction mixture and an organic solvent in an amount 0.5 to 2 times by weight as much as the above-mentioned water. It is preferable from an industrial viewpoint to use the aqueous phase containing DMSO, which has been obtained in the second liquid-liquid extraction as will be described hereinafter, as the water to be used in this stage.

Examples of the acid to be used as a pH regulator include organic acids selected from among formic acid, acetic acid, propionic acid, oxalic acid, succinic acid, benzoic acid, citric acid, maleic acid, malic acid, tartaric acid and lactic acid. Among these acids, lactic acid and citric acid are particularly preferably used. The pH regulator is used in such an amount as to give a pH value of the aqueous phase falling within the range as specified above. The pH regulator is generally employed in an amount of from 0.1 to 3.0 equivalents, preferably from 0.5 to 1.5 equivalents to the alkali catalyst used in the reaction between sucrose and the fatty acid alkyl ester.

It is desirable from the viewpoint of the operation stability that the extraction of the reaction mixture according to the present invention is effected in the presence of a salting-out agent. In the present invention, the reaction system contains a small amount of a neutralization salt originating in the neutralization of the alkali catalyst employed in the reaction with the pH regulator. However it is preferable to further add a salting-out agent. While the salting-out agent may be arbitrarily selected, it is preferable to use, for example, an alkali metal salt or an alkaline earth metal salt of the organic acid employed for regulating the pH value. By taking the safety and stability of the SE as an additive for foods, drugs, dish detergents, feeds, etc. and the interface-forming performance thereof at the extraction into consideration, it is preferable to use an alkali citrate or an alkali lactate as the salting-out agent. The extraction is performed generally at a salting-out agent concentration of 50 ppm or more, preferably from 500 to 3,000 ppm, from the viewpoints of the operation stability and the economics.

Examples of the device to be used in the first liquid-liquid extraction in the present invention include a mixer settler extractor, a counter-current derivative extraction column, a non-mixing plate extraction column, and a mixing plate extraction column. It is usually preferable from the viewpoints of the economics to use a mixer settler extractor therefor. The mixer settler extractor can be used in the multi-plate extraction system. By taking the amount of the water to be used and the economics into consideration, the extraction system preferably consists of 1 to 3 plates. The extraction is performed at a temperature lower than the boiling point of the selected organic solvent under atmospheric pressure, for example, 20° to 80° C.

After the completion of the first liquid-liquid extraction as described above, the organic solvent solution containing the SE and the aqueous solution containing DMSO are separated. The unreacted sucrose and the neutralization salt contained in the reaction mixture are mostly extracted into the aqueous phase.

in the present invention, the above-mentioned organic solvent solution is further subjected to the second liquid-liquid extraction wherein it comes in contact with water to thereby remove DMSO, etc. remaining in the organic solvent solution. The water to be used in this stage preferably has a pH value of 3 to 6.5. It is therefore preferable to previously add such a pH regulator as described above thereto.

This second liquid-liquid extraction is performed by the continuous counter-current system with the use of an extraction column wherein the SE-containing organic solvent solution obtained by the first liquid-liquid extraction is used as a light liquid while water is used as a heavy liquid. Examples of the extraction column to be used in the second liquid-liquid extraction include mixing plate extraction columns such as a Scheiber column, a rotating disc extraction column (RDC), an Ordoschouraschton column (a Miksco column), a Graessor extractor (RTL extractor), an ARD column (Luwa extractor), a Couni column, a pulsating perforated plate column, a shaking plate column, and an alternative pulsating flow extractor may be cited. Among these extraction columns, a rotating disc extraction column (RDC) is particularly preferable from the viewpoints of the extraction of DMSO, the formation of the interface, and the industrial operation stability. The rotating disc extraction column usually consists of at least 10 column plates. When the efficiency of the removal of the DMSO remaining in the SE-containing organic solvent solution and the industrial economics are taken into consideration, it is preferable that this extraction column consists of from 50 to 200 column plates. The rotating speed of the rotating disc usually ranges from about 5 to 50 rpm. The operation temperature of the second liquid-liquid extraction may be almost the same as that employed in the first liquid-liquid extraction. In the second liquid-liquid extraction, the aqueous phase is usually used in an amount of from 0.2 to 5 times by weight the amount of the organic solvent phase. Similar to the case of the first liquid-liquid extraction, it is preferable that the aqueous phase contains from 500 to 3,000 ppm of a salting-out agent.

This second liquid-liquid extraction is preferably performed in such a manner as to reduce the concentration of the DMSO remaining in the SE-containing organic solvent solution to 5 ppm or below, in particular, 1 ppm or below.

The target SE is recovered from the organic solvent solution obtained in the second liquid-liquid extraction in a usual manner. For example, the organic solvent solution is distilled using a distillation column and the organic solvent is distilled off from the column top while the target SE is recovered from the column bottom. The conditions for distillation may be, for example, the column top temperature of 70° to 80° C. and the pressure of 52 to 55 kPa.

It is industrially advantageous and thus preferable to use the aqueous solution containing DMSO, etc., which has been collected in the second liquid-liquid extraction, as a part of the extractant to be used in the first liquid-liquid extraction.

The SE thus recovered can be used as a product as such for various purposes. In order to use as an additive for foods, cosmetics, drugs, feeds, etc., it is sometimes preferable to further purify the SE. When a trace amount of an organic solvent may produce a problem, for example, the organic solvent in a trace amount can be eliminated from the SE by steam distillation, and the like method. After the completion of the steam distillation, the SE containing water can be used as an aqueous SE solution product to be added to, for example, foods, cosmetics, and drugs. Further, the aqueous SE solution product may be concentrated, evaporated to dryness, and ground to give a highly pure SE powder which is contaminated with not more than 1 ppm of DMSO and not more than 0.1% by weight of sucrose.

The present invention will be described in more detail with reference to the following Examples and Comparative Examples, but the present invention is not construed as being limited to them. In the following Examples and Comparative Examples, all parts and percentages are by weight.

EXAMPLE 1

Synthesis of SE 100 parts of sucrose and 321 parts of DMSO were fed into a reactor and heated to boil DMSO under a pressure of 2.67 KPa. After refluxing for 20 minutes, some portion of the vapor was distilled off from the system to thereby eliminate water in the reaction system. When about 40 parts of DMSO had been distilled off from the system, the distillation of the vapor was terminated. At this point, the liquid in the system contained about 0.06% by weight of water. 20 parts of methyl palmitate and about 0.31 parts of anhydrous potassium carbonate as a catalyst were then introduced into the reactor. The reactants were allowed to react while boiling DMSO at about 90° C. under a pressure of 2.67 KPa for 3 hours. The conversion of methyl palmitate exceeded 99%.

After the completion of the reaction, 0.68 parts (1.72 equivalents to the catalyst) of a 50% aqueous solution of lactic acid was added to thereby neutralize the catalyst. The reaction mixture thus obtained was composed of 70% of DMSO, 19.6% of the unreacted sucrose, 9.5% of the SE, and 0.9% of other matters. The results of an analysis on the SE composition by gel permeation chromatography indicated that it composed of 81.0% of monoester, 16.9% of diester and 2.1% of triester. The conversion of methyl palmitate calculated from the amount of the residual methyl palmitate determined by gas chromatography was 99.7%. The reaction mixture was fed into an evaporator and DMSO was evaporated at 90° C. under a pressure of 1.73 KPa. Thus a composition composed of 30% of DMSO, 46% of the unreacted sucrose, 22% of the SE, and 2% of other matters was obtained.

First Liquid-Liquid Extraction

The above-mentioned composition, isobutanol, and water (containing 1,200 ppm of potassium lactate) were fed into a mixer settler extractor and extracted at 60° C. under the atmospheric pressure. The composition of the total liquid was 7.7% of DMSO, 29% of isobutanol, 46% of the water, 5.6% of the SE, and 11.7% of the unreacted sucrose. The pH value of the aqueous phase at this stage was 6.3.

In the course of the first liquid-liquid extraction, an aqueous solution (composed of 10% of DMSO, 8% of isobutanol, 79% of water, 2% of sucrose, 0.7% of the SE and 0.3% of other matters) recovered from the rotating disc extraction column as described hereinbelow was used instead of the water. In this case, the composition of the total liquid was 10.8% of DMSO, 9.6% of sucrose, 4.4% of the SE, 28.8% of isobutanol, 45.8% of water, and 0.6% of other matters.

The isobutanol solution collected from the mixer settler was composed of 9.9% of DMSO, 41.8% of isobutanol, 37.5% of water, 2.0% of sucrose, 8.6% of the SE, and 0.2% of other matters. The extraction ratio of the SE into the isobutanol solution was 99.5%. The aqueous solution was composed of 55.1% of water, 11.8% of DMSO, 14.3% of isobutanol, 17.9% of sucrose, and 0.9% of other matters and had a pH value of 6.4.

Second Liquid-Liquid Extraction

Into a rotating disc extraction column (number of column plates: 120, rotating speed: 20 rpm) were fed the isobutanol solution obtained above from the bottom and water containing 1,200 ppm of potassium lactate from the top to perform counter-current extraction at 60° C. under the atmospheric pressure. The isobutanol solution was fed into the column in an amount of 1.81 part per part of water.

The isobutanol solution effusing from the top of the column was composed of 60% of isobutanol, 26% of water, and 14% of the SE, and contained less than 0.1% of sucrose and less than 1 ppm of DMSO.

The above-mentioned isobutanol solution was distilled at a column top temperature of 80° C. under a pressure of 55.3 KPa. Thus the isobutanol was distilled off from the column top, and the SE of a high purity was recovered from the column bottom. The obtained SE was contaminated with less than 0.1% of sucrose and less than 1 ppm of DMSO.

COMPARATIVE EXAMPLE 1

The procedure of the first liquid-liquid extraction in the above Example 1 was repeated except for adding no 50% aqueous solution of lactic acid to the reaction mixture. As a result, the aqueous phase had a pH value of 10.2. The isobutanol solution collected from the mixer settler was composed of 9.9% of DMSO, 41.9% of isobutanol, 37.6% of water, 2.0% of sucrose, and 8.4% of the SE. The SE showed a low extraction ratio of 98.1%.

EXAMPLE 2

The synthesis of SE and the first liquid-liquid extraction were conducted in the same manner as Example 1 except that the distillation of DMSO was controlled so as to adjust the DMSO concentration of the reaction mixture to be subjected to the first liquid-liquid extraction to each level as defined in Table 1 below. Then the partition ratio of each of the components in the isobutanol phase (the upper phase) and the aqueous phase (the lower phase) was determined. Table 1 summarizes the results.

TABLE 1

| DMSO concentration in reaction mixture (%) | Upper phase/ lower phase | DMSO partition ratio (%) | Sucrose partition ratio (%) | SE partition ratio (%) |
|---|---|---|---|---|
| 12 | upper | 37.8 | 7.8 | 99.9 |
| 12 | lower | 62.2 | 92.2 | 0.1 |
| 30 | upper | 42.6 | 7.9 | 99.9 |
| 30 | lower | 57.4 | 92.2 | 0.1 |
| 40 | upper | 47.2 | 13.1 | 99.5 |
| 40 | lower | 52.8 | 86.9 | 0.5 |
| 50 | upper | 54.8 | 18.4 | 95.8 |
| 50 | lower | 45.2 | 81.6 | 4.2 |

As these results show, an increase in the DMSO concentration of the reaction mixture to be subjected to the first liquid-liquid extraction promoted the partition of DMSO and the unreacted sucrose into the isobutanol phase and elevated the partition ratio of the SE into the aqueous phase.

COMPARATIVE EXAMPLE 2

60 g of the DMSO solution containing 30% of DMSO and 22% of SE, which was subjected to the first liquid-liquid extraction in Example 1, 113 g of isobutanol, and 113 g of water were mixed together and stirred at 60° C. for 15 minutes. Then the mixture was allowed to stand for 30 minutes to thereby divide into phases. The isobutanol solution (the upper phase) was concentrated under reduced pressure to thereby remove isobutanol and water to obtain a crude SE. The crude SE contained 12.8% of DMSO.

100 g of isobutanol and 100 g of water containing 1,500 ppm of potassium lactate were added to the crude SE obtained above. After stirring, allowing to stand and concentrating the upper phase each in the same manner as above, the DMSO concentration in the SE thus obtained was measured. As a result, the DMSO concentration was 5.1%. Although these procedures were repeated 10 times, the DMSO concentration in the SE could not be lowered to 5 ppm. Table 2 shows the results.

TABLE 2

| Number of extraction | Concentration of DMSO in SE (%) |
|---|---|
| 0 | 30 |
| 1 | 12.8 |
| 2 | 5.1 |
| 5 | 0.40 |
| 10 | 0.006 |

What is claimed is:

1. A process for producing a sucrose fatty acid ester wherein said sucrose fatty acid ester is recovered from a reaction mixture prepared by reacting sucrose with a fatty acid alkyl ester in the presence of an alkali catalyst by using dimethyl sulfoxide as a reaction solvent, said process comprising:

(i) subjecting said reaction mixture to a first liquid-liquid extraction by using a hardly water-miscible organic solvent, which is selected from the group consisting of an alcohol having at least 4 carbon atoms and a ketone having at least 4 carbon atoms, and water as extractants, and regulating the pH value of the aqueous phase to 3 to 7.5, to thereby extract dimethyl sulfoxide in said reaction mixture into said aqueous phase, and said sucrose fatty acid ester into the organic solvent phase;

(ii) subjecting the organic solvent solution containing said sucrose fatty acid ester obtained as the organic solvent phase in the first liquid-liquid extraction to a second liquid-liquid extraction by a continuous counter-current system using water, to thereby extract the dimethyl sulfoxide remaining in said organic solvent solution into the aqueous phase, thus giving an organic solvent solution which is substantially free from dimethyl sulfoxide; and (iii) recovering said sucrose fatty acid ester from said organic solvent solution.

2. A process as claimed in claim 1, wherein said fatty acid alkyl ester is a $C_1$ to $C_4$ alkyl ester of a saturated or unsaturated fatty acid having 6 to 30 carbon atoms.

3. A process as claimed in claim 1, wherein said dimethyl sulfoxide reaction solvent is used in an amount of from 20 to 150% by weight based on the total amount of said sucrose and said fatty acid alkyl ester.

4. A process as claimed in claim 1, wherein said alkali catalyst is an alkali metal carbonate or an alkali metal hydroxide.

5. A process as claimed in claim 4, wherein said alkali catalyst is used in an amount of from 0.001 to 0.1 equivalent to said fatty acid alkyl ester.

6. A process as claimed in claim 1, wherein said hardly water-miscible organic solvent used in said first liquid-liquid extraction is n-butanol and/or isobutanol.

7. A process as claimed in claim 1, wherein the concentration of dimethyl sulfoxide in said reaction mixture to be subjected to said first liquid-liquid extraction is from 20 to 50% by weight.

8. A process as claimed in claim 1, wherein said organic solvent is used in said first liquid-liquid extraction in an amount of from 1 to 10 parts by weight per part by weight of said sucrose fatty acid ester in said reaction mixture, and water is used in said first liquid-liquid extraction in an amount of from 0.5 to 2 parts by weight per part by weight of said organic solvent.

9. A process as claimed in claim 1, wherein a pH regulator employed for controlling the pH value of said aqueous phase in said first liquid-liquid extraction is an organic acid.

10. A process as claimed in claim 9, wherein said organic acid is lactic acid, citric acid or a mixture thereof.

11. A process as claimed in claim 1, wherein said aqueous phase in the first liquid-liquid extraction contains from 500 to 3,000 ppm of a salting-out agent.

12. A process as claimed in claim 1, wherein the operation temperature of said first liquid-liquid extraction is from 20° to 80° C.

13. A process as claimed in claim 1, wherein in said second liquid-liquid extraction, said aqueous phase is used in an amount of from 0.2 to 5 times by weight the amount of said organic solvent solution.

14. A process as claimed in claim 1, wherein said aqueous phase in said second liquid-liquid extraction contains from 500 to 3,000 ppm of a salting-out agent.

15. A process as claimed in claim 1, wherein said aqueous phase containing dimethyl sulfoxide obtained in said second liquid-liquid extraction is used as a part of said water as an extractant in said first liquid-liquid extraction.

16. A process as claimed in claim 1, wherein the concentration of dimethyl sulfoxide in said organic solvent solution obtained in said second liquid-liquid extraction is not more than 5 ppm.

17. A process as claimed in claims 1, wherein said second liquid-liquid extraction is performed in a rotating disc extraction column.

18. A process as claimed in claim 17, wherein said rotating disc extraction column used in said second liquid-liquid extraction consists of from 50 to 200 plates and the rotating speed thereof is from 5 to 50 rpm.

19. A process as claimed in claim 1, wherein said organic solvent solution obtained in said second liquid-liquid extraction is distilled using a distillation column, and thus an organic solvent contained in said organic solvent solution is distilled off from a column top while and said sucrose fatty acid ester is recovered from a column bottom.

20. A process as claimed in claim 19, wherein said sucrose fatty acid ester thus recovered through distillation is contaminated with not more than 1 ppm of dimethyl sulfoxide and not more than 0.1% by weight of sucrose.

* * * * *